United States Patent
Uutela et al.

(10) Patent No.: US 7,038,601 B2
(45) Date of Patent: May 2, 2006

(54) ARTIFACT REMOVAL FROM AN ELECTRIC SIGNAL

(75) Inventors: Kimmo Henrik Uutela, Helsinki (FI); Tor Börje Rantala, Helsinki (FI); Juha Petri Virtanen, Helsinki (FI)

(73) Assignee: Instrumentatium Corp., Helsinki (FI)

( * ) Notice: Subject to any disclaimer, the term of this patent is extended or adjusted under 35 U.S.C. 154(b) by 2 days.

(21) Appl. No.: 10/724,347

(22) Filed: Nov. 26, 2003

(65) Prior Publication Data
US 2004/0135571 A1    Jul. 15, 2004

(30) Foreign Application Priority Data
Nov. 29, 2002    (EP)    .................................. 02396178

(51) Int. Cl.
*H03M 1/06*    (2006.01)
(52) U.S. Cl. .................................................. 341/118
(58) Field of Classification Search ................ 341/118, 341/120, 155, 141, 143; 600/508, 509; 455/63.1
See application file for complete search history.

(56) References Cited

U.S. PATENT DOCUMENTS

| | | | |
|---|---|---|---|
| 4,243,045 A | 1/1981 | Maas | 600/508 |
| 4,483,346 A * | 11/1984 | Slavin | 600/523 |
| 4,991,580 A | 2/1991 | Moore | 600/509 |
| 5,038,785 A | 8/1991 | Blakeley et al. | 600/484 |
| 5,269,302 A * | 12/1993 | Swartz et al. | 607/45 |
| 5,341,811 A * | 8/1994 | Cano | 600/508 |
| 5,365,428 A | 11/1994 | dePinto et al. | |
| 5,921,939 A * | 7/1999 | Danielsson et al. | 600/509 |
| 5,924,980 A * | 7/1999 | Coetzee | 600/300 |
| 6,041,250 A | 3/2000 | DePinto | |

FOREIGN PATENT DOCUMENTS

| | | |
|---|---|---|
| EP | 0 470 764 | 2/1992 |
| EP | 0 738 496 | 10/1996 |
| WO | WO-02/13689 | 2/2002 |

OTHER PUBLICATIONS

European Search Report Nov. 10, 2003. Applicant's communication to EPO. Amended European application.

* cited by examiner

*Primary Examiner*—Peguy JeanPierre
(74) *Attorney, Agent, or Firm*—Andrus, Sceales, Starke & Sawall, LLP

(57) ABSTRACT

The invention relates to a method and apparatus for suppressing interference in an electric signal, particularly for suppressing interference in an electrocardiogram (ECG) signal in connection with magnetic resonance imaging (MRI). In order to improve the accuracy of the suppression, the electric signal is first sampled at a high sampling frequency, whereby a first sequence of samples is obtained. Some of the samples in the first sequence of samples are then selected on the basis of predetermined criteria. The first sequence is then downsampled using the selected samples, whereby a second sequence of samples is obtained. The second sequence forms a digital presentation of the electric signal in which the interference is suppressed.

24 Claims, 3 Drawing Sheets

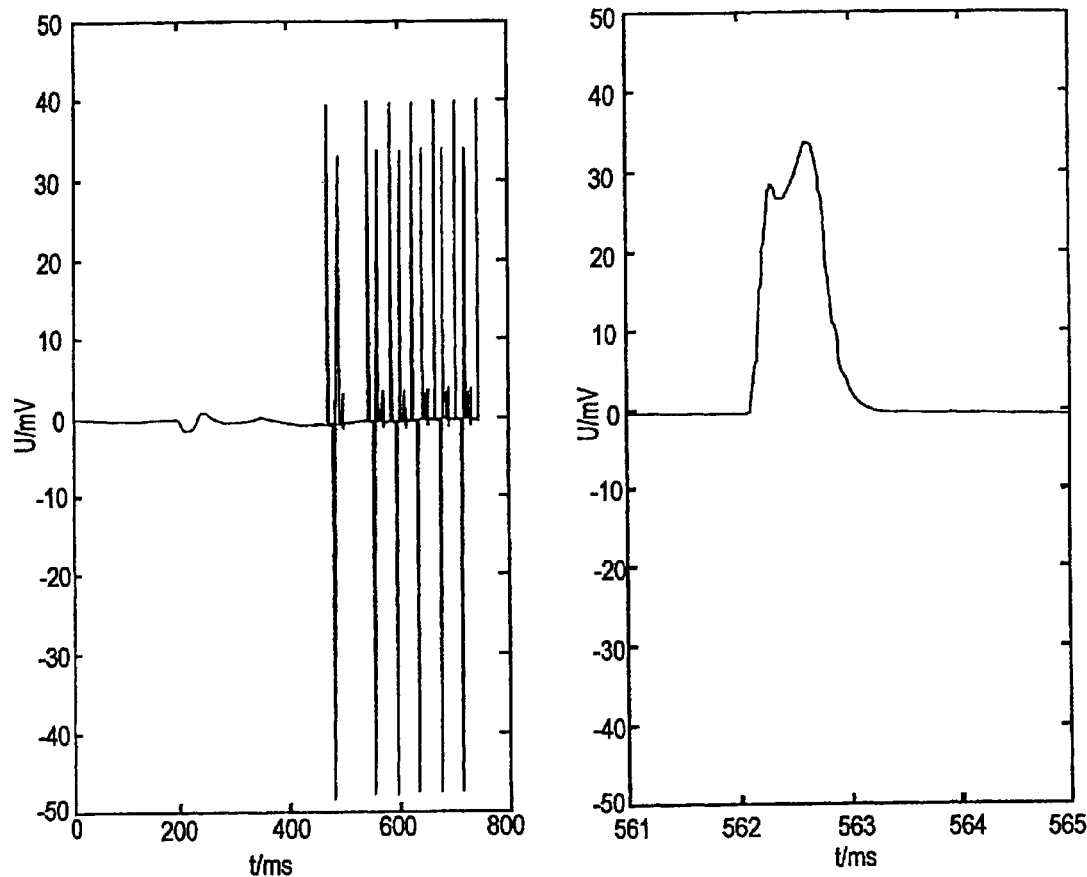
FIG. 1a PRIOR ART FIG. 1b
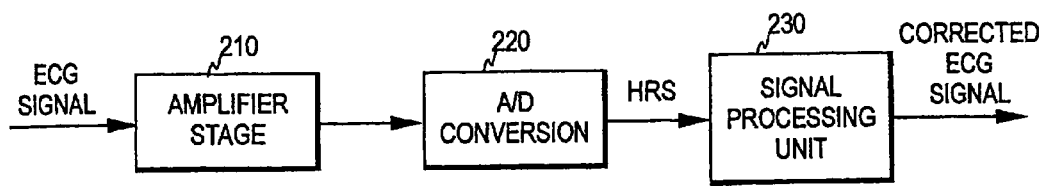
FIG. 2

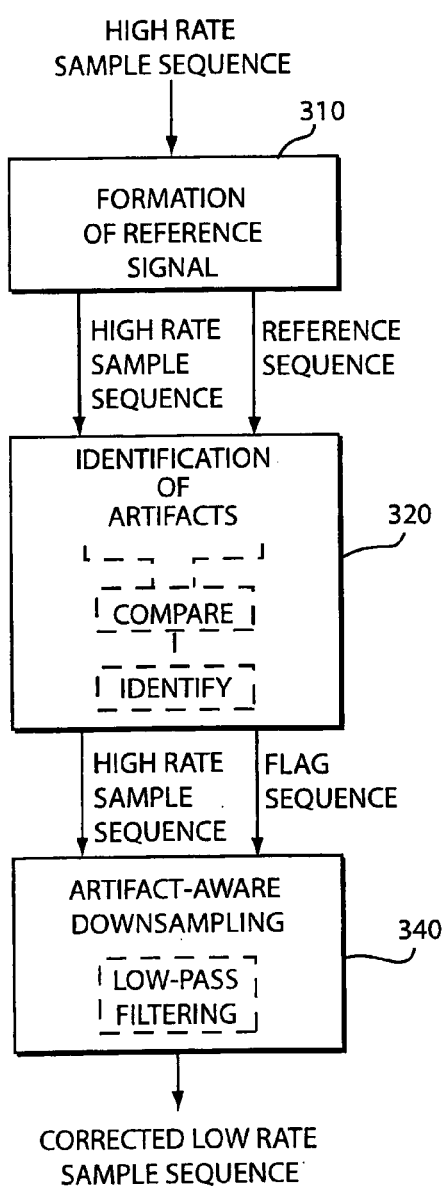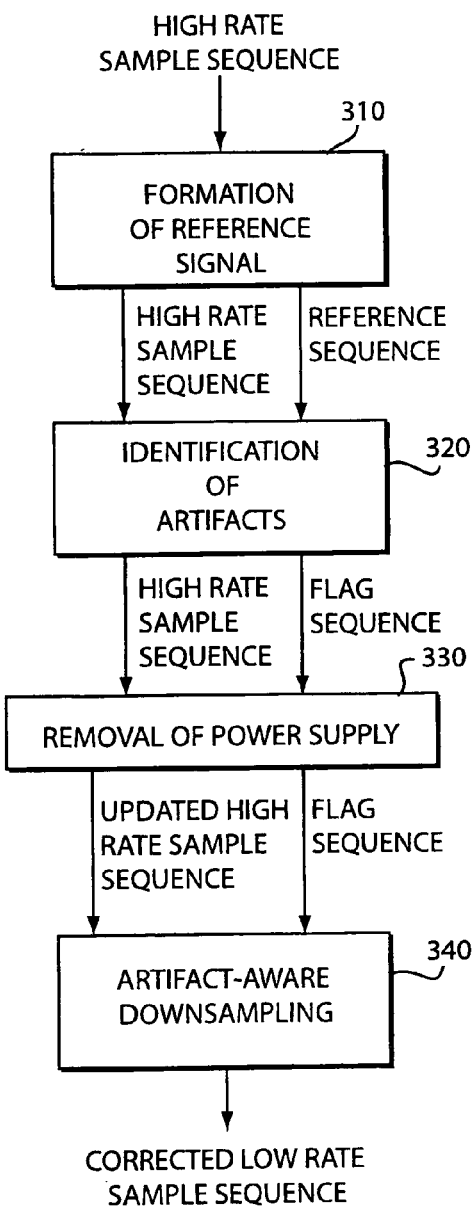
FIG. 3a
FIG. 3b

ARTIFACT REMOVAL FROM AN ELECTRIC SIGNAL

CROSS REFERENCE TO RELATED APPLICATION

The present application claims priority from European Patent Application No. 02396178.2, filed Nov. 29, 2002.

FIELD OF THE INVENTION

The present invention relates generally to a method and apparatus for suppressing or removing artifacts from an electric signal. The term "artifact" here refers to interference which has a certain structure and is therefore not noise-like random interference. The invention is intended especially for medical technology to eliminate artifact components from an electrocardiogram (ECG) signal in connection with magnetic resonance imaging (MRI), but the method can be applied to any systems in which an artifact component similar to the one caused by an MRI device to an ECG signal is superimposed on a useful signal. Artifact components are typically caused by sources which are external to the apparatus receiving the useful signal.

BACKGROUND OF THE INVENTION

As is known, MRI (Magnetic Resonance Imaging) is a technique used for getting images of a body without the use of X-rays. In MRI, the patient is placed within a rapidly changing magnetic field created by the MRI device. Radio waves are simultaneously transmitted to the patient, and images of the interior of the body are obtained by means of a computer analysis of the radio waves received from the patient.

During the imaging, the condition of the patient is constantly monitored. This includes the monitoring of the ECG signal of the patient, for example. One drawback related to the monitoring is that the intense magnetic fields of the imaging device induce interference with the ECG signal of the patient. This interference, which is termed here an artifact, is short-termed and strong, and appears very frequently.

FIGS. 1a and 1b show a typical example of the narrow and strong interference peaks caused to the ECG signal by MRI measurement. FIG. 1a illustrates a sequence of the narrow interference pulses superimposed on the ECG signal, while FIG. 1b illustrates the shape and length of one interference pulse. The artifact is usually rather similar for each MR image acquired and consists of a few short peaks. The shape of an interference peak is roughly box-like, with a relatively constant period between the steepest rise and fall edges.

The prior art methods intended for suppressing the above-described artifacts are based on either limiting the rise and fall speed of the ECG signal or freezing the signal during the interference periods. In the following these prior art methods are discussed briefly.

A natural way of detecting the MRI gradient peaks is to monitor the rise and/or fall speed, i.e. the slew rate, of the ECG signal. A solution based on a slew rate limiter is disclosed in U.S. Pat. No. 4,991,580. This patent presents a method whereby the ECG signal is supplied to the input of a slew rate limiter (SRL) circuit, which limits the slew rate of the ECG to a pre-selected maximum value slightly greater than a typical maximum slew rate in an ECG signal.

Another approach for eliminating MRI induced artifacts superimposed on an ECG signal is presented in U.S. Pat. No. 5,038,785. This patent describes a cardiac monitor in connection with an MRI device, the monitor to include a comparator which compares each wave form received from the ECG electrodes with the properties of a cardiac signal, such as the slope. When the comparator detects interference in the ECG signal, it gates a track and hold circuit. The track and hold circuit passes the ECG signal, except when gated by the comparator. When gated by the comparator, the track and hold circuit continues to supply the same output voltage it had at the beginning of the gating period, i.e. it freezes the ECG signal for the period of interference.

U.S. Pat. No. 4,243,045 presents a method for the suppression of narrow interference pulse peaks and of interference hum in a useful signal. The method is intended particularly for suppressing the pacemaker pulses and the power supply hum superimposed on an ECG signal. The narrow pulses caused by the pacemaker are blanked out by keeping the signal constant for the blanking-out period, and the power supply hum is eliminated by an interference hum filter. The filtered-out interference hum component is opposingly superimposed on the original signal to compensate for the interference hum.

The prior art methods based on freezing the signal entail the fundamental drawback of not being able to take into account signal changes occurring during the freezing period. The methods based on limitation of the slew rate, in turn, involve the fundamental drawback that some of the interference remains in the useful signal, as the methods limit only the size of the interference. For these reasons, the prior art methods may leave errors of substantial magnitudes affecting the useful signal.

It is the objective of the invention to improve the accuracy of the methods described above and to bring about a new and efficient solution for suppressing or eliminating artifacts from a useful signal, particularly MRI-induced artifacts from an ECG signal.

SUMMARY OF THE INVENTION

The objective of the present invention is to bring about a solution for eliminating as accurately as possible narrow interference peaks from a useful signal, such as MRI-induced artifacts from an ECG signal.

According to the invention, the useful signal is first sampled at a high sampling frequency. The samples are then supplied to an artifact detection process during which the degraded samples are identified, i.e. it is detected which of the samples are degraded by the artifact and which are essentially free of artifact and thus good samples. The selected high quality samples of the useful signal are then utilized in a subsequent downsampling process, which is in this context termed an artifact-aware downsampling, since the preceding detection process indicates the samples containing an artifact component. More particularly, in the downsampling process, samples considered as free of artifact are used to generate a new sequence of samples having a sampling frequency substantially lower than the original sampling frequency. By utilizing the artifact-free samples only, the downsampling process thus constructs a new sample sequence with a reduced sampling rate. Consequently, the method of the invention includes a controlled downsampling of the original signal, the downsampling being controlled by the artifact-content of the high rate sample sequence.

Thus one aspect of the invention is providing a method for suppressing interference in an electric signal, the method comprising the steps of sampling the electric signal at a first sampling frequency, whereby a first sequence of samples is obtained, selecting some of the samples in the first sequence of samples on the basis of predetermined criteria, and downsampling said first sequence using the selected samples, whereby a second sequence of samples is obtained, the second sequence forming a digital presentation of the electric signal in which the interference is suppressed.

The method of the invention improves the accuracy of artifact elimination, since it does not limit or freeze the signal values. Instead, the signal is sampled at a high rate, the artifact-content of the samples is detected, and the detected artifact content controls the downsampling of the signal so that only high quality samples are utilized.

Another aspect of the invention is that of providing an apparatus for suppressing interference in an electric signal, the apparatus comprising sampling means for sampling the electric signal at a first sampling frequency, whereby a first sequence of samples is obtained, selection means for selecting some of the samples in the first sequence on the basis of predetermined criteria, and downsampling means, operatively connected to the selection means, for downsampling the first sequence by using the selected samples, whereby a second sequence of samples is obtained, the second sequence forming a digital presentation of the electric signal in which the interference is suppressed.

In a preferred embodiment of the invention, the samples of the first sequence are compared with a reference signal generated from the original useful signal, whereby the selecting step is performed based on the comparing step.

In a further preferred embodiment of the invention, information about the artifact content of the samples is generated as a result of the comparison of the signal with the reference. The information generated is supplied, together with the samples, to the downsampling process, where the signal is downsampled using this information. The information consists preferably of a sequence of flags, each flag being attached to the relevant sample and indicating where the sample is artifact-free or not.

In another preferred embodiment of the invention, the power supply hum, possibly appearing at 50 or 60 Hz and superimposed on the ECG signal, is eliminated from the ECG signal before the downsampling process. This is implemented by first calculating the amount of power supply hum in the ECG signal by using the artifact-free samples only. The calculated value of the hum at each sample is then deducted from the corresponding sample, whereby updated sample values are obtained for the high rate sample sequence. In this way the power supply hum appearing in the signal can be efficiently removed. Thus one advantage of the method of the invention is that it allows simultaneous and efficient suppression of both MRI induced artifacts and power supply hum.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIGS. 2 to 3c in the appended drawings, wherein:

FIG. 1a illustrates the artifact superimposed on an ECG signal in connection with magnetic resonance imaging (MRI), FIG. 1b illustrates one artifact pulse in FIG. 1a, FIG. 2 illustrates the apparatus according to the invention, FIG. 3a illustrates one embodiment of the method of the invention, FIG. 3b illustrates a second embodiment of the method of the invention.

DETAILED DESCRIPTION OF THE INVENTION

Figure 3C:
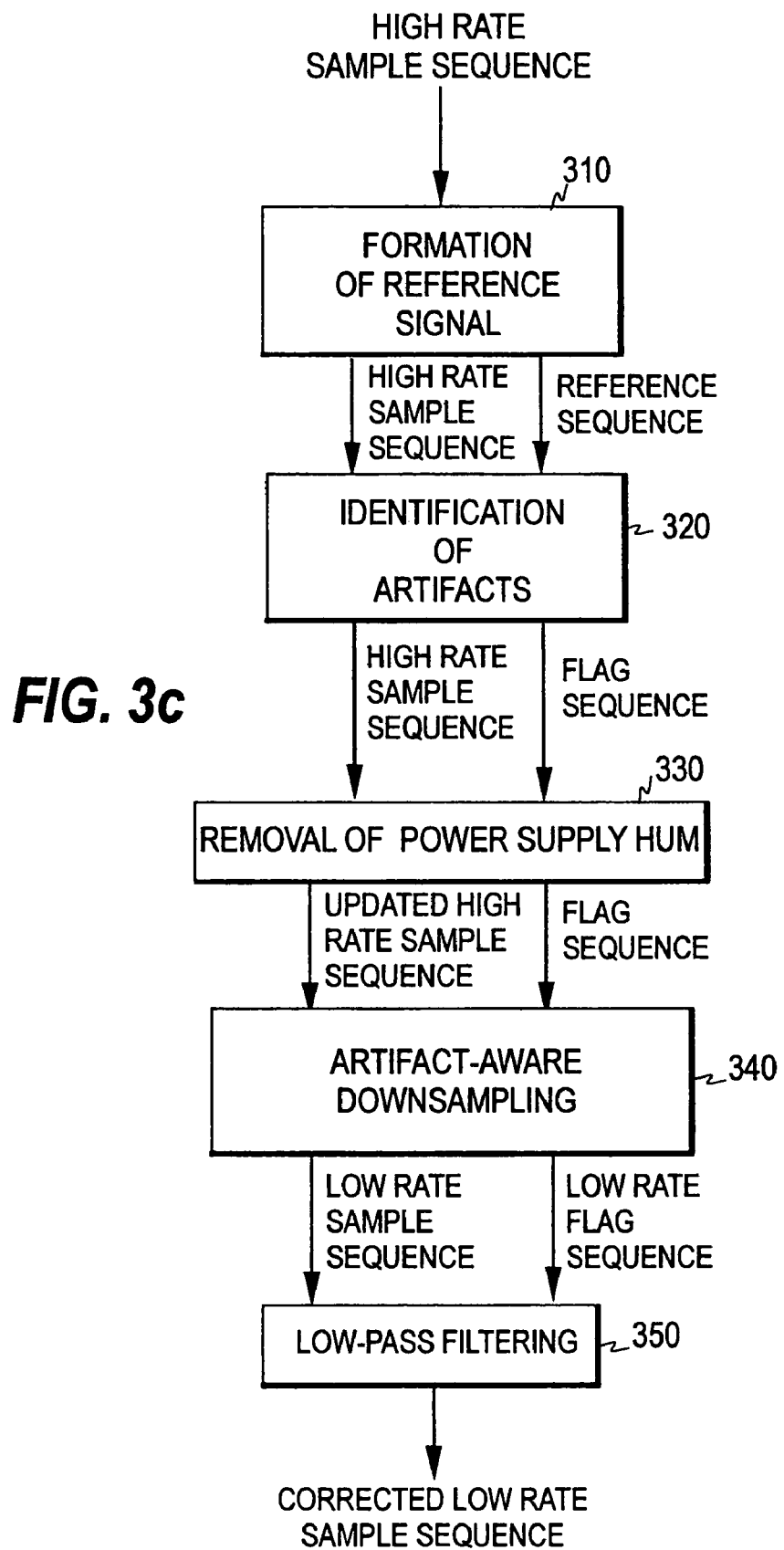
FIG. 3c illustrates a third embodiment of the method of the invention.

FIG. 2 is a schematic presentation of the apparatus according to the present invention. The signal received from the ECG sensor(s) is supplied to an amplifier stage 210, which amplifies the signal before it is sampled and converted into digitized format in an A/D converter 220. A high sampling rate is used in the A/D converter to sample the ECG signal. A typical sampling rate could be of the order of 10 kHz, for example, which yields about 10 samples during one interference peak (cf. FIG. 1b). In any case, the initial sampling rate used in the present invention is higher than the sampling rate needed for the original signal, the latter being typically 100 to 1000 Hz in the case of an ECG signal.

As a result of the sampling, a high rate sample sequence HRS is obtained, which is buffered and processed in a digital signal processing unit 230. The processing unit performs the removal of the artifacts and outputs the corrected ECG signal, i.e. the original ECG signal from which the artifacts have been removed.

FIG. 3a illustrates one embodiment of the method performed in the digital signal processing unit 230. A separate reference signal is first formed from the high rate sample sequence HRS (step 310). This reference signal is preferably generated from the sample sequence itself, through the use of a slew rate limiter, for example. In other words, the reference signal is preferably generated by copying the input signal and limiting the slew rate in the copy. The reference signal serves as a reference for identifying the artifact in the original input signal.

Instead of being generated from the input signal, the reference signal may also be an external signal, i.e. a signal which is not derived from the ECG signal input to the signal processing unit. The MRI device, for example, can provide an external reference signal whose high amplitude levels identify the samples containing an artifact component. In view of the invention, the actual method of generating the reference signal is not essential.

The samples of the input signal containing an artifact component are then identified (step 320). Although these samples can be identified by comparing an external reference signal, such as the above-mentioned signal provided by the MRI device, to a predetermined threshold, it is assumed here that the said samples are identified by comparing the input signal, i.e. the original ECG signal, with the reference signal generated from the original ECG signal by limiting the slew rate. The comparison is performed by comparing each sample of the input signal to the corresponding sample of the reference signal. When a sample of the input signal meets predefined criteria, it is considered as an artifact-free sample. Different criteria may be used in determining when a sample is artifact-free. In this example, when the input signal and the reference signal are within the noise level of each other, the sample is considered artifact-free and thus valid.

Based on the comparison process at step 320, some of the high rate samples are selected and the selected samples are forwarded for a downsampling process. In the embodiment of FIG. 3a, the selection is implemented as follows. First, on the basis of the results of the comparison process, information is generated about the validity of each sample of the input signal. This information preferably consists of a sequence of flags, one flag being attached to each sample of the input signal, to indicate whether the corresponding sample is valid (i.e. free from an artifact). Second, the samples and the associated flags are forwarded for the downsampling process, during which the digital input signal is downsampled utilizing the information about the validity of the samples, i.e. the flag sequence (step 340). As the information about the artifact content of the samples, i.e. the flag sequence, is forwarded for the downsampling process, the process is here called artifact-aware downsampling. Based on the information, only artifact-free samples are selected, and the downsampling is performed based on these samples only.

It is to be noted here that it is preferred not to discard the samples affected by artifacts before entering the downsampling process, but instead all the samples are supplied for said process, together with the flag sequence, so that the downsampling process receives the information about the locations in the time domain of the good and bad samples. Another alternative is to discard the samples which are identified as having been affected by artifacts and to supply only the good samples for the downsampling process. However, this alternative requires that the significant moments corresponding to the good samples are forwarded for the downsampling process.

The actual downsampling can be performed in many ways, which are known in the art. For integer downsampling ratios, the most common approach is to use an anti-aliasing low-pass filter and then to select every $n^{th}$ sample. For non-integer downsampling ratios, the signal is usually first upsampled by padding the signal with zeros, the signal is then low-pass filtered, and then the desired samples are selected (every $n^{th}$ sample). To keep the individual sample rate changes small, the whole process is often divided up into several stages with smaller sampling rate ratios.

Another approach used for downsampling is interpolation: the signal at the correct point in time is calculated by modeling the neighboring values. Methods typically used are to select the value of the nearest neighbor or to model the signal using a polynomial function or spline.

As a result of the downsampling, a new sample sequence with a lower sample rate is obtained. The sample rate of this sequence can be 300 Hz, for example. The new sequence forms the digital presentation of the ECG signal from which the artifact has been removed.

FIG. 3b illustrates a preferred embodiment of the method performed in the digital signal processing unit. In addition to the functions described in connection with FIG. 3a, this embodiment includes the elimination of power supply hum, i.e. elimination of the interference at 50 or 60 Hz caused by a power supply. In the artifact-aware downsampling described above, each output sample is based on input samples having very small artifact levels. However, since the good samples are taken from varying parts of the time window, the output may have a disturbance resembling temporal jitter in the sampling. This will deform the signal slightly, whereby the signal can interfere with a notch filter intended to remove the 50/60 Hz power supply hum. Therefore, better results can be achieved by using the solution of FIG. 3b, where the power supply hum is removed before downsampling (step 330). The elimination can be implemented by estimating the amplitude and phase of the power supply hum and removing the estimated hum from the input signal, i.e. subtracting the estimated hum from the original signal. The estimation is implemented by using only the samples considered as good ones when calculating the amplitude and phase of the power supply hum. Thus in the process of removing power supply hum, the information about the artifact content of the samples is utilized, similarly as in the downsampling process. The power hum estimate can be calculated by means of a band-pass filter, which is thus an artifact-aware filter as it uses the good samples only.

When the downsampling process comprises a FIR filter, the artifact-aware downsampling can be obtained by calculating the weighted averages of only the good samples with their normal weights and by correcting the gain based on the weights of the bad samples. For example, if the FIR filter is a boxcar filter, the artifact-aware downsampling process, i.e. the filter, calculates the average of the corresponding good samples, said average to form the value of one low rate sample.

When the downsampling process includes interpolation, the standard interpolation means can be applied by taking into account the good samples and the corresponding moments in the time domain.

In a further preferred embodiment of the invention, the above-mentioned artifact-aware downsampling is combined with artifact-aware low-pass filtering. The filter can be replaced by an artifact-aware FIR filter using the number of good samples as the flag. This kind of implementation further improves the accuracy of the apparatus, and it may also be more tolerant to long periods of noise.

Low-pass filtering may be a separate step subsequent to downsampling, or it may be divided into two stages, of which the first one is formed by the above-mentioned low-pass filtering in the downsampling process. The second stage may then occur after the downsampling, whereby the filtering in the second stage is applied to the lower rate sample sequence. The division of low-pass filtering into two stages is advantageous in terms of calculating power; the processing time is shorter if the filtering is divided into two stages of which the first one provides rough filtering and the second one is a more accurate stage. The use of low-pass filtering is illustrated in FIG. 3c. The low-pass filtering stage 350 of receiving the low rate sample sequence and the corresponding low rate flag sequence can thus form the only low-pass filtering stage of the apparatus or it can complement the low-pass filtering performed at stage 340.

By using more than one bit in the flag, an indication may be given of the magnitude of the artifact contained in the sample. In this way the artifact components can be classified into several categories depending on their magnitude. As the quality of a low rate sample calculated depends on the number of high rate samples used to produce it, the flag sequence supplied for stage 350 can be numeric, and the FIR filter can be implemented by using all the samples but having different weights for each sample.

The artifact-aware FIR filter may be implemented according to equation (1), for example:

$$y = \frac{\sum_i f_i b_i x_i \times \sum_i b_i}{\sum_i f_i b_i} \quad (1)$$

where x is the input signal, b is the filter coefficient vector, and f is the flag sequence vector. A binary flag sequence is represented with zeros for bad samples and with ones for good samples.

The artifact-aware band-pass filter producing the estimated power supply hum sequence at step 330 may be implemented according to equation (2), for example:

$$y_p = A(FA)^+ Fx \quad (2)$$

where the elements of the n×2 matrix A are $A_{i,1} = \sin(2\pi i/n)$ and $A_{i,2} = \cos(2\pi i/n)$, F is a diagonal matrix having the flag sequence as the diagonal elements, $(.)^+$ is the Moore-Penrose pseudoinverse, and x is the input signal.

Although the invention was described above with reference to the examples shown in the appended drawings, it is obvious that the invention is not limited to these, but may be modified by those skilled in the art without departing from the scope and spirit of the invention. Even if the method was described with reference to the MRI-induced artifact superimposed on the ECG signal, the method can be applied to any system in which an artifact component with like properties is superimposed on a useful signal.

The invention claimed is:

1. A method for suppressing interference in an electrical signal, the method comprising the steps of:
    sampling the electrical signal at a first sampling frequency to obtain a first sequence of samples;
    identifying some of the samples in the first sequence of samples on the basis of predetermined criteria; and
    downsampling at least the identified samples of said first sequence to obtain a second sequence of samples from the identified samples of said first sequence, the second sequence of samples forming a digital presentation of the electrical signal in which the interference is suppressed.

2. A method according to claim 1 further comprising the step of generating information about the interference content in the samples and wherein the identification step is further defined as identifying samples in the first sequence of samples on the basis of their interference content.

3. A method according to claim 2 wherein the generating step is further defined as attaching a flag to each of the samples to indicate whether the sample is free of interference or not.

4. A method according to claim 3 wherein the downsampling is carried out using samples with a flag indicating that the corresponding sample is free of interference.

5. The method according to claim 4 further defined as providing all samples of said first sequence of samples for downsampling.

6. The method according to claim 2 wherein the identifying step is further defined as identifying samples that are artifact free.

7. The method according to claim 2 further defined as providing the identified samples for downsampling to form said second sequence of samples.

8. A method according to claim 1 further comprising the step of comparing the samples of the first sequence with a reference signal and wherein the identification step is performed based on the comparing step.

9. A method according to claim 8 further comprising the step of forming the reference signal from the first sequence of samples by limiting a slew rate in the sequence.

10. A method according to claim 8 wherein said reference signal comprises an external reference signal.

11. A method according to claim 1 wherein the downsampling step is further defined as downsampling the identified samples.

12. The method according to claim 1 wherein a frequency of downsampling is less than said first sampling frequency.

13. A method according to claim 1 wherein the downsampling step includes low pass filtering of the first sequence of samples.

14. A method according to claim 1 further comprising the step of low pass filtering the second sequence of samples.

15. A method according to claim 1 further comprising the step of suppressing power supply hum in the first sequence of samples by updating values of the samples according to the amount of power supply hum.

16. A method according to claim 15 wherein the suppressing step includes the steps of:
    estimating the power supply hum based on the first sequence of samples; and
    deducting the estimated power supply hum from the first sequence to update the values of the samples.

17. A method according to claim 1 further defined as one for suppressing interference in an ECG electric signal.

18. An apparatus for suppressing interference in an electrical signal, the apparatus comprising:
    sampling means for sampling the electrical signal at a first sampling frequency to obtain a first sequence of samples;
    identification means for identifying some of the samples in the first sequence of samples on the basis of predetermined criteria; and
    downsampling means operatively connected to said identification means for downsampling at least the identified samples of said first sequence to obtain a second sequence of samples from the identified samples of said first sequence and for forming a digital presentation of the electrical signal in which the interference is suppressed from said second sequence of signals.

19. An apparatus according to claim 18 wherein the identification means is further defined as identifying samples in the first sequence of samples on the basis of their interference content.

20. An apparatus according to claim 19 wherein the identification means is further defined as identifying samples that are artifact free.

21. An apparatus according to claim 18 wherein said identification means further comprises means for comparing the samples of the first sequence with a reference signal so that the identification is based on the comparison.

22. An apparatus according to claim 18 wherein the downsampling means is further defined as downsampling the identified samples.

23. An apparatus according to claim 18 wherein said downsampling means is further defined as carrying out said downsampling at a frequency of downsampling that is less than said first sampling frequency.

24. An apparatus according to claim 18 further comprising:
    means for estimating the power supply hum based on the first sequence of samples; and
    means for updating the samples of the first sequence based on the estimated amount of power supply hum.

* * * * *